(12) United States Patent
Tsukamoto

(10) Patent No.: US 10,070,836 B2
(45) Date of Patent: Sep. 11, 2018

(54) X-RAY MAMMOGRAPHY SYSTEM

(71) Applicant: CANON KABUSHIKI KAISHA, Tokyo (JP)

(72) Inventor: Takeo Tsukamoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 15/022,860

(22) PCT Filed: Sep. 10, 2014

(86) PCT No.: PCT/JP2014/004660
§ 371 (c)(1),
(2) Date: Mar. 17, 2016

(87) PCT Pub. No.: WO2015/040830
PCT Pub. Date: Mar. 26, 2015

(65) Prior Publication Data
US 2016/0220209 A1     Aug. 4, 2016

(30) Foreign Application Priority Data

Sep. 19, 2013    (JP) ................................. 2013-193905

(51) Int. Cl.
*A61B 6/00*        (2006.01)
*H01J 35/08*      (2006.01)
*H05G 1/00*      (2006.01)

(52) U.S. Cl.
CPC ............ *A61B 6/502* (2013.01); *A61B 6/4021* (2013.01); *H01J 35/08* (2013.01); *H01J 2235/087* (2013.01); *H05G 1/00* (2013.01)

(58) Field of Classification Search
CPC .......... A61B 6/00; A61B 6/4021; A61B 6/502
USPC .......................................................... 378/37
See application file for complete search history.

(56) References Cited

U.S. PATENT DOCUMENTS

| | | | |
|---|---|---|---|
| 2009/0129549 A1 | 5/2009 | Virshup | |
| 2012/0051496 A1 | 3/2012 | Wang et al. | |

FOREIGN PATENT DOCUMENTS

| | | |
|---|---|---|
| JP | 2007-097610 A | 4/2007 |
| JP | 2011-504647 A | 2/2011 |
| JP | 2013-504365 A | 2/2013 |

*Primary Examiner* — Jurie Yun
(74) *Attorney, Agent, or Firm* — Canon USA, Inc. I.P. Division

(57) ABSTRACT

An X-ray mammography system including an X-ray detecting unit and an X-ray generating unit. The X-ray detecting unit includes a detecting portion that detects X-rays that have passed through a breast. The X-ray generating unit includes a transmission type target and an electron emitting source and is configured to radiate X-rays toward the detecting portion when irradiated with electrons. The transmission type target has a target layer having an electron incidence surface. The distance between a normal to the target layer and a distal end, which is an end of an X-ray irradiated region of the detecting portion closer to the chest of the testee, is larger than the distance between the normal and a proximal end, which is an end of the X-ray irradiated region far away from the chest.

10 Claims, 4 Drawing Sheets

[Fig. 1]
(a)
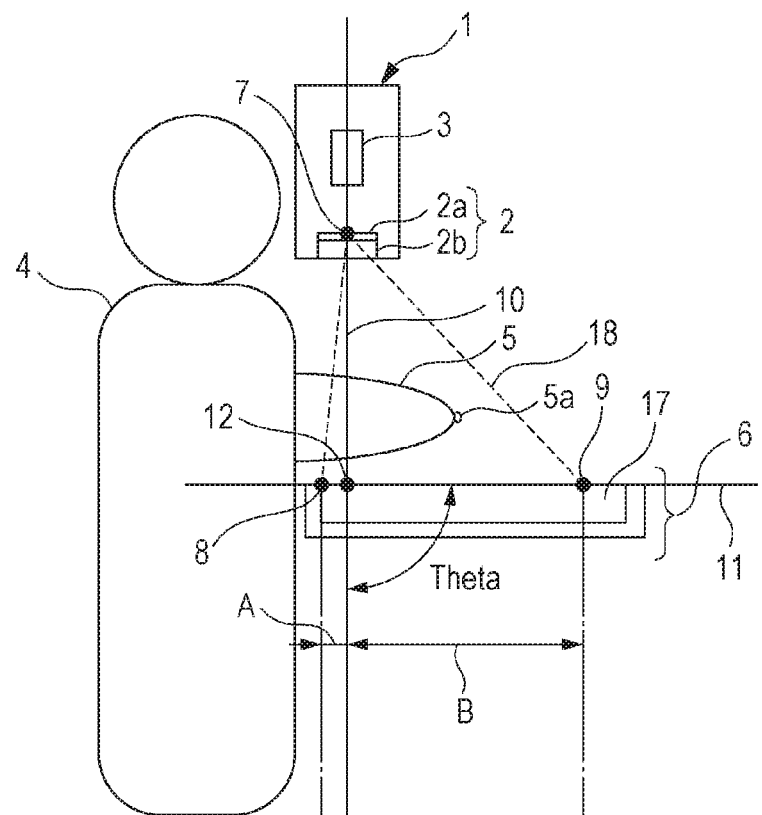
(b)
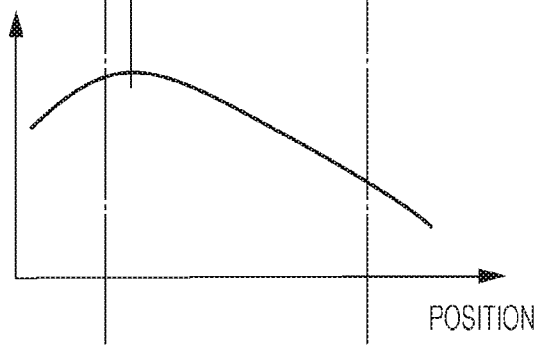

[Fig. 2]
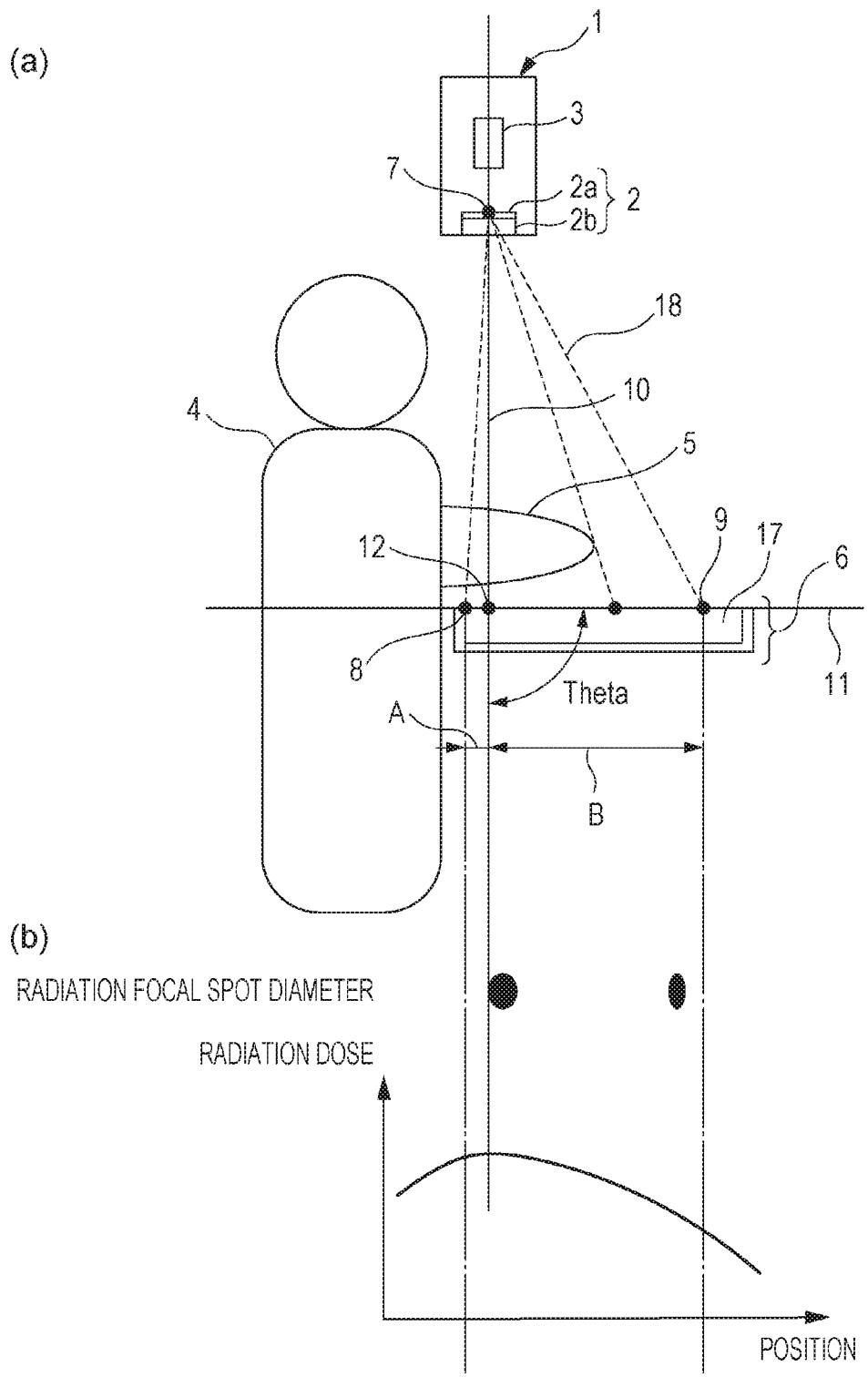

[Fig. 3]
(a)
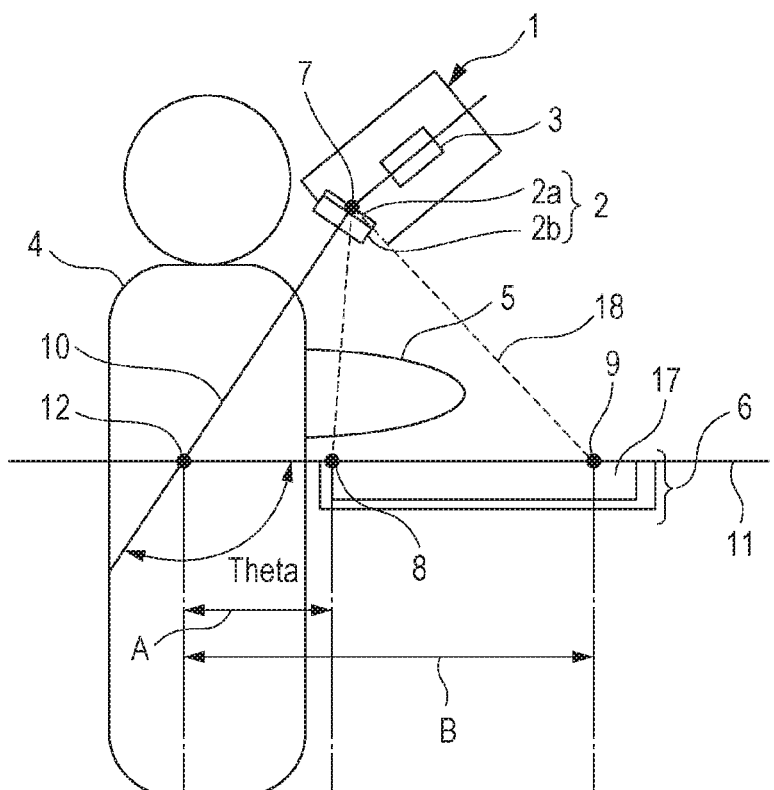
(b)
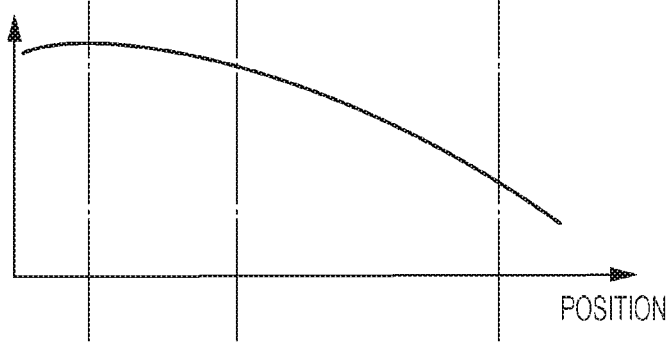

[Fig. 4]
(a)
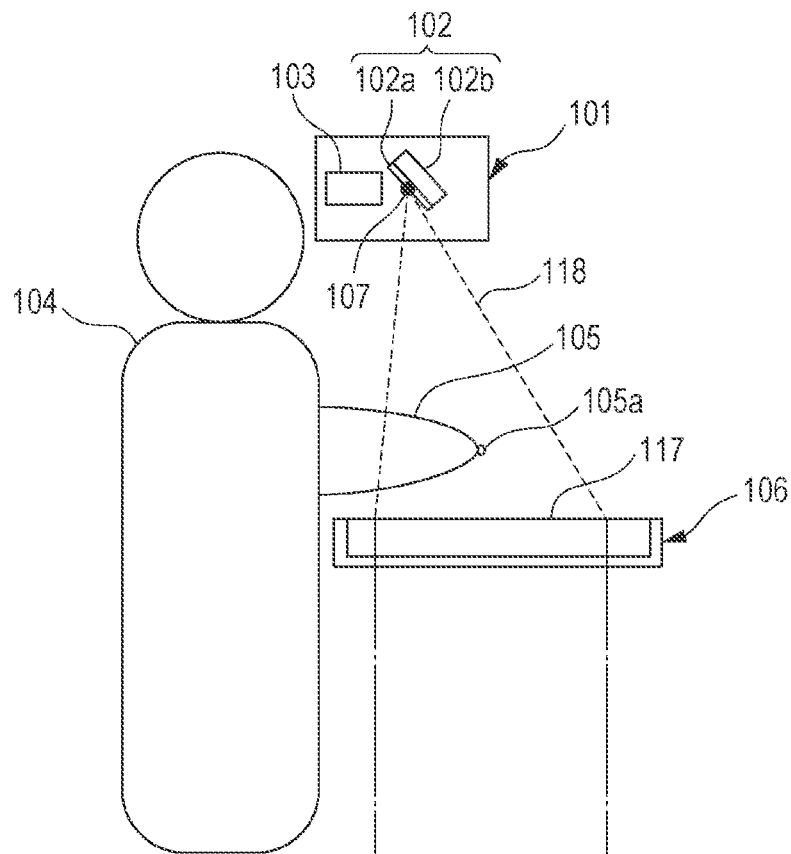
(b)
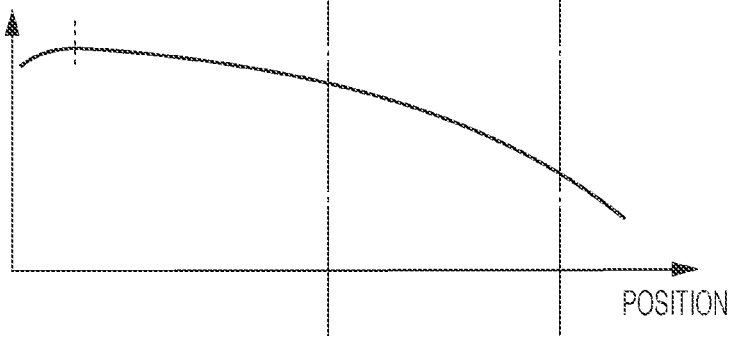
-Prior Art-

X-RAY MAMMOGRAPHY SYSTEM

TECHNICAL FIELD

The present invention relates to an X-ray mammography system.

BACKGROUND ART

A known example of X-ray mammography systems is disclosed in PTL 1, which includes a reflection type X-ray tube as an X-ray generating unit.

FIG. 4(a) illustrates the basic configuration of an X-ray mammography system 101 that includes a reflection type X-ray tube as an X-ray generating unit.

In FIG. 4(a), the X-ray generating unit 101 includes a target 102 and an electron emitting source 103. The target 102 is a reflection type target in which a target layer 102a that generates X-rays when irradiated with an electron beam is provided on a supporting substrate 102b that reflects X-rays. The radiation area of X-rays 118 generated when the target layer 102a is irradiated with an electron beam emitted by the electron emitting source 103 is defined by a collimator (not shown), and thus, a predetermined X-ray irradiated area is formed on a detecting portion 117 of an X-ray detecting unit 106 through a breast 105 of a testee 104.

The X-ray generating unit 101 is generally disposed such that the electron emitting source 103 is close to the testee 104, as shown in FIG. 4(a). Such placement causes the focal spot center 107 of the X-rays 118 to be viewed from a nipple 105a side at a larger angle than the chest side. This makes an apparent focal spot diameter of the X-rays 118 at the nipple 105a side smaller than that at the chest side, thus enhancing the resolution. This allows early detection of a calcified region, which tends to occur in the nipple 105a. Furthermore, this can increase radiation dose on the chest, where the distance of transmission of the X-rays 118 is large, thereby preventing a decrease in radiation dose on the chest.

CITATION LIST

Patent Literature

PTL 1: Japanese Translation Patent Publication No. 2011-50467

SUMMARY OF INVENTION

Technical Problem

However, in the case of the reflection type X-ray generating unit 101 including the reflection type target 102, the electron emitting source 103 is located at the side of X-ray radiation from the target 102. Thus, the electron emitting source 103 is located between the target 102 and the testee 104. This makes it difficult to dispose the focal spot center 107 of the X-rays 118, which is the center of generation of the X-rays 118 (the center of an electron-beam irradiated area on the target layer 102a), close to the testee 104. This poses a problem in that a blind area, which is formed in the vicinity of the chest of the testee 104 and is not irradiated with the X-rays 118, so that an image cannot be acquired, is prone to increase. Reversing the positional relationship between the target 102 and the electron emitting source 103 from that shown in FIG. 4(a) could solve the above problem, but a change in the diameter of the focal spot of the X-rays 118 and a change in radiation dose are also reversed from the above, thus causing a problem in that good image-acquisition conditions are difficult to obtain.

Solution to Problem

The present invention is made in consideration of the problem of the related art and provides an X-ray mammography system in which the blind area can be reduced while satisfying good image-acquisition conditions.

The present invention provides an X-ray mammography system including an X-ray detecting unit including a detecting portion configured to detect X-rays that have passed through a breast; and an X-ray generating unit including a transmission type target and an electron emitting source and configured to radiate X-rays toward the detecting portion. The transmission type target includes a target layer having an electron incidence surface. The transmission type target generates X-rays when irradiated with electrons and radiates the X-rays in a direction opposite to the electron incidence surface. The electron emitting source emits an electron beam to the target layer. The distance between a normal to the target layer and a distal end, which is an end of an X-ray irradiated region of the detecting portion closer to a chest of a testee, is larger than the distance between the normal and a proximal end, which is an end of the X-ray irradiated region far away from the chest.

The present invention also provides an X-ray mammography system including an X-ray detecting unit including a detecting portion configured to detect X-rays that have passed through a breast; and an X-ray generating unit including a transmission type target and an electron emitting source and configured to radiate X-rays toward the detecting portion. The transmission type target includes a target layer having an electron incidence surface. The transmission type target generates X-rays when irradiated with electrons and radiates the X-rays in a direction opposite to the electron incidence surface. The electron emitting source emits an electron beam to the target layer. An apparent focal spot of X-rays radiated to the detecting portion through a nipple is smaller than an apparent focal spot of X-rays radiated to the detecting portion through the breast except the nipple.

Further features of the present invention will become apparent from the following description of exemplary embodiments with reference to the attached drawings.

Advantageous Effects of Invention

Since the present invention employs a transmission X-ray generating unit including a transmission type target, an electron-beam emitting source is located at the back with respect to the direction of X-rays radiated from the target. This prevents the electron-beam emitting source from interfering with setting the target close to the testee, making it easy to place the target close to the testee. This allows a configuration in which the focal spot center of X-rays is close to the testee, thereby minimizing the blind area. Furthermore, an apparent focal spot diameter of X-rays at the nipple can be smaller than that at the chest, and the radiation dose at the chest can be higher than that at the nipple. This can provide good conditions for enhancing the resolution at the nipple and increasing the radiation dose at the chest where the X-ray transmission distance is large.

BRIEF DESCRIPTION OF DRAWINGS

FIG. 1 includes part (a) illustrating the configuration of an X-ray mammography system according to a first embodiment of the present invention, and part (b) showing a change in X-ray focal spot diameter and a change in radiation dose in the first embodiment.

FIG. 2 includes part (a) illustrating the configuration of an X-ray mammography system according to a second embodiment of the present invention, and part (b) showing a change in X-ray focal spot diameter and a change in radiation dose in the second embodiment.

FIG. 3 includes part (a) illustrating the configuration of an X-ray mammography system according to a third embodiment of the present invention, and part (13) showing a change in X-ray focal spot diameter and a change in radiation dose in the third embodiment.

FIG. 4 includes part (a) illustrating the configuration of an X-ray mammography system of the related art, and part (b) showing a change in X-ray focal spot diameter and a change in radiation dose in the related art.

DESCRIPTION OF EMBODIMENTS

An X-ray mammography system according to embodiments of the present invention will now be described with reference to the drawings, in the drawings, like signs denote like components.

First Embodiment

FIG. 1(a) illustrates the placement of a mammography system of a first embodiment and a testee 4 in a virtual plane including a focal spot center 7, which is the center of the focal spot of an electron beam formed on a target 2, and a normal 10 perpendicular to a target layer 2a. In FIG. 1(a), an X-ray generating unit 1 includes the target 2 and an electron emitting source 3. The X-ray generating unit 1 of the present invention is a transmission X-ray tube. The target 2 is a transmission type target in which the target layer 2a that generates X-rays when irradiated with an electron beam is provided on a supporting substrate 2b that transmits X-rays. The radiation area of X-rays 18 generated when the target layer 2a is irradiated with an electron beam emitted by the electron emitting source is defined by a collimator (not shown) disposed between the target 2 and a breast 5 of the testee 104, and thus, a predetermined X-ray irradiated area is formed on a detecting portion 17 of an X-ray detecting unit 6 through the breast 105. In this description, a virtual plane including the detecting portion 17 is hereinafter referred to as a detection plane 11. In the drawings, the broken lines indicate a space in which an X-ray beam 18 collimated by the collimator is radiated. The X-ray beam 18 radiated from the X-ray generating unit 1 toward the X-ray detecting unit 6 forms on X-ray irradiated area of a predetermined shape on the detecting portion 17. Examples of the shape of the X-ray irradiated area include a rectangular shape and a trapezoidal shape.

The target 2 is disposed such that the target layer 2a faces the electron emitting source 3. The X-rays generated when the target layer 2a is irradiated with an electron beam emitted from the electron emitting source 3 are released through the supporting substrate 2b. The target layer 2a may be a metal layer with an atomic number of 42 or greater or a layer containing the metal so as to efficiently generate X-rays. Specific examples are tungsten, tantalum, and molybdenum. An example of the supporting substrate 2b is a diamond substrate.

The electron emitting source 3 is an electron gun, which generally includes a cathode, a grid electrode, and a lens electrode (not shown). X-rays can be generated by irradiating the target layer 2a with electrons extracted from the cathode through the grid electrode and then undergoing acceleration and convergence through the lens electrode. An example of the cathode is a thermionic cathode.

The X-ray beam 18 is radiated toward the detection plane 11 of the X-ray detecting unit 6 through the breast 5 of the testee 4 and reaches the detecting portion 17 of the X-ray detecting unit 6. An X-ray shadow of the breast 5 of the testee 4 is detected by the X-ray detecting unit 6, and thus, an X-ray radiograph including mammary glands, fat, and so on in the breast 5 is acquired. A mammogram can be acquired in this way.

Next, the relationship between the X-ray irradiated area and the testee 4 will be described with reference to FIG. 1(a), in FIG. 1(a), the X-ray irradiated area is indicated as a line segment defined with a proximal end 8 and a distal end 9, which are at different distances from the testee 4, is formed on the detection plane 11. The proximal end 8 is a closest end of an X-ray irradiated region of the detecting portion 17 with regard to a distance from the chest of the testee 4. The distal end 9 is a farthest end of an X-ray irradiated region of the detecting portion 17 with regard to a distance from the chest of the testee 4. A point of intersection of a normal 10 extending from a focal spot center 7 and the detection plane 11 is defined as a reference point 12. The reference point 12 is a point at which the size of an apparent focal spot viewed from the detection plane 11 is the maximum. The size of the apparent focal spot on the detection plane 11 decreases with increasing distance from the reference point 12. The X-ray mammography system of this embodiment of the present invention is characterized in that the distance A between the reference point 12 and the proximal end 8 and the distance B between the reference point 12 and the distal end 9 have a relationship of distance A<distance B. An angle theta that the normal 10 in the X-ray radiating direction with respect to the detection plane 11 forms with the detection plane 11 opposite to the testee 4 with respect to the reference point 12 is preferably 90 degrees or more and less than 180 degrees. The angle theta in this embodiment is 90 degrees.

FIG. 1(b) quantitatively shows a change n X-ray focal spot diameter and a change in radiation dose between the proximal end 8 and the distal end 9 of the X-ray detecting unit 6 in the case of setting for distance A<distance B. As shown in FIG. 1(b), the focal spot diameter decreases with increasing distance from the proximal end 8 to the distal end 9. The radiation dose decreases with increasing distance from the proximal end 8 to the distal end 9. Decreasing the focal spot diameter at the distal end 9 to enhance the resolution at a nipple 5a makes it easy to early detect calcification that tends to occur at the nipple 5a. The intensity of X-rays radiated from the target 7 depends on the angle of inclination to the normal 10, that is, an exit angle. Thus, disposing the chest close to the proximal end 8 at which the exit angle with respect to the normal 10 is small can reduce a decrease in detection sensitivity at the chest at which the transmission distance is larger than that at the nipple 5a. The distance B is preferably twice or more the distance A to ensure the above advantages.

The size of the blind area depends on the positional relationship between the focal spot center 7 and the testee 4. To decrease the blind area, the focal spot center 7 needs to be as close as possible to the testee 4. In the transmission X-ray generating unit 1, the electron emitting source 3 can be disposed at the opposite side from the X-ray radiating direction with respect to the target 2. This can reduce interference of the electron emitting source 3 in setting the focal spot center 7 close to the testee 4, thus making it relatively easy to achieve a configuration in which the distance between the focal spot center 7 and the testee 4 is small.

Second Embodiment

A second embodiment will next be described with reference to FIGS. 2(a) and 2(b). The second embodiment is configured to further decrease the blind area described in the first embodiment shown in FIG. 1(a). Specifically, the X-ray generating unit 1 is located above the head of the testee 4 so that the components of the X-ray generating unit 1 around the target 2 are not in contact with the testee 4 even if the planar distance between the focal spot center 7 and the testee 4 is decreased. This can further decrease the planar distance between the focal spot center 7 and the testee 4, thereby reducing the blind area.

Third Embodiment

A third embodiment will next be described with reference to FIGS. 3(a) and 3(b). In the third embodiment, the target 2 is disposed at an angle no that the normal 10 to the surface of the target layer 2a at the focal spot center 7 extended in the X-ray radiating direction is inclined to a direction intersecting the testee 4. The angle theta in this case is preferably 100 degrees or more and 160 degrees or less. The angle theta in this example is 130 degrees. The electron emitting source 3 is disposed at a position far away from the testee 4 with respect to the normal 10 extending toward the electron emitting source 3. Inclining the target 2 in this manner makes it easier to place the focal spot center 7 close to the testee 4 than the first embodiment in which the target 2 is disposed in a horizontal position. Placing the electron emitting source 3 far away from the testee 4 can prevent the electron emitting source 3 from interfering with setting the focal spot center 7 close to the testee 4.

While the present invention has been described with reference to exemplary embodiments, it is to be understood that the invention is not limited to the disclosed exemplary embodiments. The scope of the following claims is to be accorded the broadest interpretation so as to encompass such modifications and equivalent structures and functions.

This application claims the benefit of Japanese Patent Application No. 2013-193905, filed Sep. 19, 2013, which is hereby incorporated by reference herein in its entirety.

The invention claimed is:

1. An X-ray mammography system comprising:
an X-ray detecting unit including a detecting portion configured to detect X-rays passed through a breast; and
an X-ray generating unit including a transmission type target and an electron emitting source and is configured to radiate X-rays toward the detecting portion, the transmission type target including a target layer having an electron incidence surface, the transmission type target configured to be irradiated with electrons and radiating the X-rays in a direction opposite to the electron incidence surface, and the electron emitting source emitting an electron beam to the target layer,
wherein a distance between a normal line of the target layer and a distal end is larger than a distance between the normal line and a proximal end, where the proximal end is associated with an end of an X-ray irradiated region in the detecting portion the closest to a chest of a testee, and the distal end is an end of the X-ray irradiated region far away from the chest of the testee, and
wherein the electron emitting source is located further away from the proximal end along the detecting portion than the transmission type target.

2. The X-ray mammography system according to claim 1, wherein the electron emitting source emits the electron beam to the target layer to form a focal spot on the target layer, and the normal line passes through a center of the focal spot.

3. The X-ray mammography system according to claim 1, further comprising a breast insertion portion between the detecting portion and the transmission type target.

4. The X-ray mammography system according to claim 1, wherein the distance between the normal line of the target layer and the distal end is twice or more the distance between the normal line and the proximal end.

5. The X-ray mammography system according to claim 1, wherein, assuming a virtual plane including the detecting portion, an angle theta that the normal line forms with the virtual plane is 90 degrees or more and less than 180 degrees.

6. The X-ray mammography system according to claim 5, wherein the angle theta that the normal line forms with the virtual plane is 100 degrees or more and 160 degrees or less.

7. The X-ray mammography system according to claim 1, wherein the transmission type target is disposed in the X-ray generating unit in such a manner that the normal line is inclined in a direction crossing the testee.

8. An X-ray mammography system comprising:
an X-ray detecting unit including a detecting portion configured to detect X-rays that have passed through a breast; and
an X-ray generating unit including a transmission type target and an electron emitting source and is configured to radiate X-rays toward the detecting portion, the transmission type target including a target layer having an electron incidence surface, the transmission type target generating X-rays when irradiated with electrons and radiating the X-rays in a direction opposite to the electron incidence surface, and the electron emitting source emitting an electron beam to the target layer,
wherein an apparent focal spot of X-rays radiated to the detecting portion through a nipple is smaller than an apparent focal spot of X-rays radiated to the detecting portion through the breast except the nipple, and
wherein the electron emitting source is located further away from a proximal end along the detecting portion than the transmission type target.

9. The X-ray mammography system according to claim 8, wherein the target layer is disposed with respect to the X-ray detecting unit so that the apparent focal spot of the X-rays radiated to the detecting portion through the nipple is the smallest.

10. The X-ray mammography system according to claim 8, wherein the X-ray generating unit is disposed with respect to the X-ray detecting unit so that the apparent focal spot of the X-rays radiated to the detecting portion through the nipple is the smallest.

* * * * *